United States Patent [19]

Koseki et al.

[11] Patent Number: 4,670,137
[45] Date of Patent: Jun. 2, 1987

[54] IMPURITY DETECTOR

[75] Inventors: Yasuo Koseki, Hitachiohta; Katsuya Ebara, Mito; Sankichi Takahashi, Hitachi; Kazuhiko Matsuoka, Takasaki; Minoru Kuroiwa, Abiko; Akira Yamada, Hitachi, all of Japan

[73] Assignee: Hitachi, Ltd., Tokyo, Japan

[21] Appl. No.: 823,004

[22] Filed: Jan. 27, 1986

[51] Int. Cl.⁴ .............................................. B01D 37/04
[52] U.S. Cl. ...................................... 210/96.1; 73/28; 73/61.3
[58] Field of Search .............. 210/239, 248, 900, 96.1, 210/180, 195.1, 196; 55/210, 212, 213, 215, 218; 73/28, 61.3

[56] References Cited
U.S. PATENT DOCUMENTS 4,041,768  8/1977  Gibert et al. ............................. 73/28
4,064,047 12/1977  Bernreiter ............................ 210/96.1
4,154,088  5/1979  Werner .................................... 73/28
4,449,816  5/1984  Kohsaka et al. ........................ 73/28
4,548,716 10/1985  Boeue .................................. 210/900

Primary Examiner—Ivars Cintins
Attorney, Agent, or Firm—Antonelli, Terry & Wands

[57] ABSTRACT

An impurity detector atomizes a liquid sample by injecting the sample into a chamber with a gas. In the chamber the liquid is heated, preferably by heating the gas prior to injection, to cause all the liquid to evaporate. The solid impurities contained in the liquid are thus entrained in the gas and carried to a detector region. The chamber is arranged so that all the gas and all the particles arrive at the detector region. A particle detector measures the number and size of the particles and from that measurement, the concentration of impurities in the sample can be determined. The system permits on-line operation, and produces accurate results.

15 Claims, 11 Drawing Figures

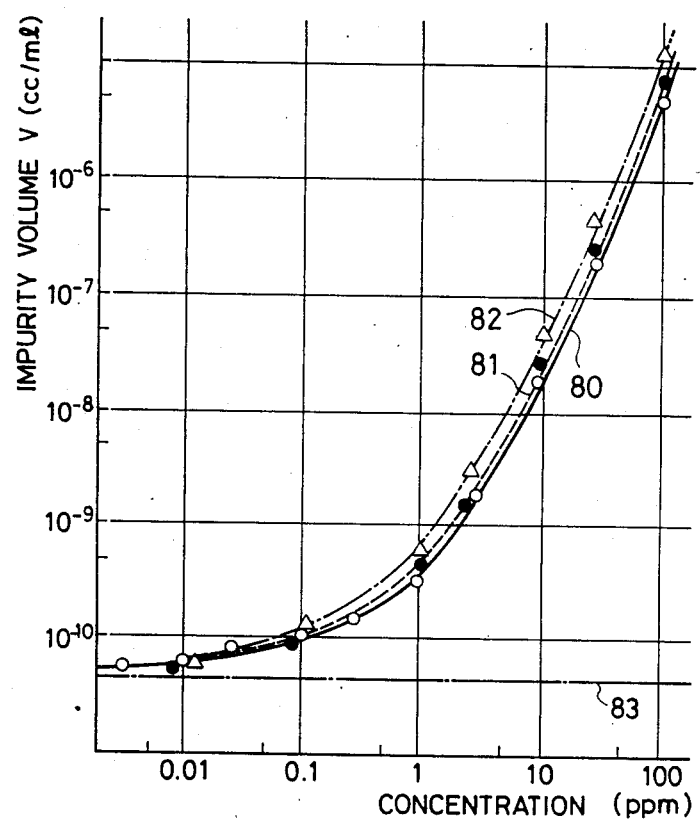

IMPURITY DETECTOR

BACKGROUND OF THE INVENTION

The present invention relates to a detector and method for detecting impurities in liquids by measuring a number and size of impurities in a liquid.

The present invention is particularly but not exclusively, concerned with the detection of impurities in high-purity water (also known as super-pure water). High-purity water is used in such fields as nuclear power generation, in the electronics industry, and in medical treatment, where it is important that the water used should have minimal amounts of organic or inorganic substances contained within it. The organic substances include, for example, soluble organic matter and insoluble microorganisms, while the inorganic substances may include soluble salts and insoluble fine particles.

The importance of using high-purity water can be seen, for example, in the context of washing of semiconductor integrated circuits. When a semiconductor integrated circuit is in water containing impurities, the impurities left on the surface of the device, may cause malfunctioning of the semiconductor integrated circuit. Thus, an increased amount of impurity in the water increases a failure rate in the produced semiconductor integrated circuits, and therefore it is desirable to use water of as high a purity as possible; however, existing techniques for determining the purity level in water, when the concentration of impurities is low, are not accurate and therefore it is difficult to predict the effect any particular water sample may have. In, for example, the Journal "Kagaku Sochi" (Chemical Apparatus), pages 81 to 84 of Jan., 1984, and "Chemical Engineering", pages 22 to 27 of Nov., 1980 methods for refining water to produce high-purity water have been proposed, wherein primary pure water is produced by filtration and by reverse osmosis, and the primary pure water is further refined by a polisher and an ultra-filter thereby resulting in high-purity water. However, since the purification methods are not 100% efficient in removing impurities, it is still necessary to determine the amount of impurities in the produced high-purity water.

In a conventional system for determining the amount of impurity present the following analysis of water at an intermediate point of a line for supplying refined water to a use point is performed. A sensor is installed in a refined water supplying pipe to detect soluble organic matter, and measurement is made by a total organic carbon (TOC) measuring instrument. Meanwhile, the soluble organic matter is similarly detected by a sensor installed in the pipe, and specific resistance is measured by an electric conductance measuring instrument, with the two measurements can be carried out on-line.

With respect to fine particles in water, a part of refined water is filtered by a filter to catch fine particles. Then, fine particles on the filter are magnified and observed by using an electron microscope so as to measure the diameter and number of the particles. Microorganisms are cultured after being caught as in the case of the measurement of fine particles, and the number of the microorganisms is measured from the colonies of the microorganisms using an electron microscope.

The measurement of fine particles and microorganisms cannot be effected on-line, and a long time and expertise are required in the measurement. For this reason, it is impossible rapidly to measure the quality of the refined water and to immediately transmit the results to the refining stage, and control the refining conditions so as to improve the water quality.

A method in which the impurities in a liquid are measured on-line by direct use of a laser is proposed in, for example, Analytical Chemistry, 45(2), 223A, 1973. However, the entire amount of impurities in the liquid cannot be measured by this proposed method. As mentioned above, the impurities contained in a liquid (in water) may include granular substances which are insoluble in water and substances dissolved in water. The granular substances may be further divided into inorganic and organic substances and the latter into microorganisms and others. The dissolved substances may also be divided into inorganic and organic substances and these two types may be further divided into electrolytes and non-electrolytes. Although the above described substances are all classified as impurities in water, it is necessary to measure all of the impurities because the above described substances are contained in high-purity water in extremely small quantities. However, substances dissolved in water cannot be measured by the laser method mentioned above.

Japanese Utility Model Publication No. 51-43086 discloses a method and apparatus for calibration of a laser particle detector by providing a gas flow containing entrained solid particles of predetermined size. A liquid containing the particles of predetermined size is injected with gas into an atomization chamber through an atomizing nozzle. Part of the atomized liquid and the gas is passed from a second nozzle into a stream of warmed gas upstream of the particle detector. The liquid evaporates in the warm gas stream to leave the particles entrained in the gas stream. The detector measures the particle size, and the measured values compared with the actual size of the particles. Atomized liquid not entering the warm gas stream returns from the atomization chamber via a drain outlet into a holding tank for the liquid to be atomized.

However, this method is not entirely accurate. Since only part of the liquid reaches the detector, it is critically important that that part must be a representative sample, which is not always the case. Furthermore, the two-part atomization and evaporation also creates the possibility of error.

The present invention seeks to provide an impurity detector, and a method of measuring impurities, which is accurate, and permits on-line operation wherein a liquid sample is atomized by injecting it with gas into a chamber, in which chamber the liquid is totally evaporated.

In accordance with advantageous features of the present invention, a liquid impurity detector is provided which includes an evaporation chamber for a liquid sample, at least one atomizer nozzle for injection of a liquid sample into the chamber with a gas, and a means for heating the liquid to effect evaporation in the evacuation chamber of all of the atomized liquid. A detector region is connected to the chamber in a substantially closed manner so that all of the gas and all of the solid impurity particles entrained in the gas due to the evaporation of the liquid passed from the chamber to the detector region, and a particle detector communicates with the detector region, with the particle detector being adapted to measure the number and size of the impurity particles in the gas.

In the accordance with further advantageous features of the present invention, a method for measuring the number and size of impurities in a liquid sample is provided, with the method including the steps of atomizing the liquid sample by injecting the liquid sample with gas into an evacuation chamber from at least one nozzle, passing the atomized liquid and gas along the chamber, with all of the liquid being evaporated in the evaporation chamber to leave solid impurity particles entrained in the gas, passing all the gas having the solid impurity particles entrained therein to a detector region, and, at the detector region, measuring the number and size of solid impurity particles in the gas by a particle detector.

Advantageously, the particle detector is a dispersed laser beam detector of the type disclosed in, for example, "Air Conditioning and Refrigeration", Jan. 1984, pages 79-81, in an article entitled "Monitoring and Measurement of Sub-micron Aerosol Particles", with the laser beam detector being capable of detecting particles having a diameter greater than 0.1 μm.

The evaporation of the liquid in the chamber is preferably achieved by pre-heating the gas before it is used to atomize the liquid, and temperatures of greater than 40° C., and preferably greater than 60° to 70° C. has been found suitable. However, it is also possible to evaporate the liquid by heating the entire chamber, by applying infra-red radiation to the atomized liquid, or applying high frequency energy to the atomized liquid to create molecular movement in the liquid.

It has been found that atomization of the liquid generally produces water droplets containing only one impurity particle, so that subsequent evaporation causes the production of a flow of discrete particles, each corresponding to one impurity, whether that impurity is based on a soluble, or an insoluble, substance present in the liquid. It then becomes possible to determine the number and size of the individual particles, thereby permitting accurate analysis of the sample.

BRIEF DESCRIPTION OF THE DRAWINGS

Embodiments of the invention will now be described in detail, by way of example, with reference to the accompanying drawings in which:

FIG. 11 is a graphical illustration of a variation of impurity volume with impurity concentration for three different water samples.

DETAILED DESCRIPTION

Figure 1:
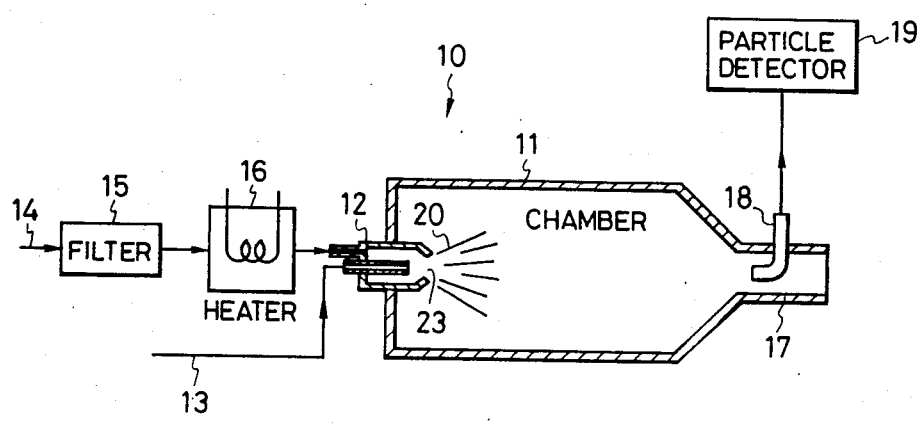
FIG. 1 is a schematic cross-sectional view of an impurity detector constructed in accordance with the present invention.

Referring now to the drawings wherein like reference numerals are used throughout the various views to designate like parts and, more particularly, to FIG. 1, according to this figure an impurity generally designated by the reference numeral detector 10 includes a chamber 11 having an inlet formed by a nozzle 12 connected to a source of pure water via an inlet conduit 13, and a source of air via a conduit 14. The conduit 14 contains a filter 15, which removes particles having a size greater than 0.1 μm from the air stream, and also contains a heater 16 which raises the temperature of the air prior to injection into the nozzle 12. A detector region is provided at an end of the chamber 11 remote from the nozzle 12, with the detector region 17 containing a duct 18 communicating with a particle detector 19 preferably using dispersed laser beams.

In use, the pure water is fed via the conduit 13 to the nozzle 12, simultaneously with heated air via the conduit 14. The pressure of the air is preferably 40 to 60 kg/cm$^2$. The mixing of the pressurized air with the water causes a jet of atomized liquid 20 to be expelled from the nozzle 12 into the chamber 11. It has been determined that the heating of air to a temperature greater than 40° C. and, preferably to a temperature greater than 60° to 70° C. causes the water droplets to evaporate in the chamber before a significantly contacting the side walls of the chamber 11. The evaporation of the liquid in the jet 20 produces a flow of particles corresponding to the impurities present in the liquid before atomization, and the pressurized air causes these particles to be carried to the detection region 17. Here, some of the particles enter the duct 18 to be detected by the detector 19, which calculates the number and diameter of the particles. From this information the total number of particles in the water sample entering the chamber 11 through the nozzle 12, can be calculated. Since the detector 19 can operate continuously, on-line measurement of the impurities in the water sample can be determined.

Figure 3:
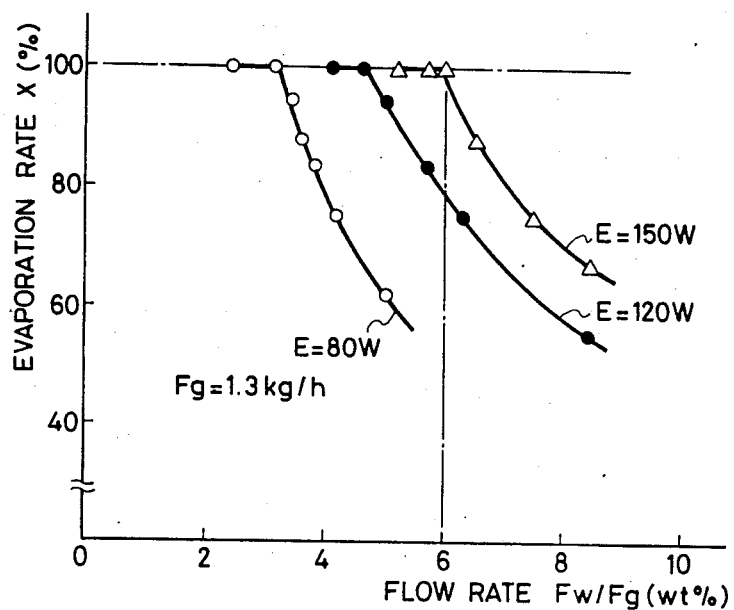
FIG. 3 is a graphical illustration of a variation of evaporation rate with respect to a weight/flow rate ratio for different heater inputs.
Figure 4:
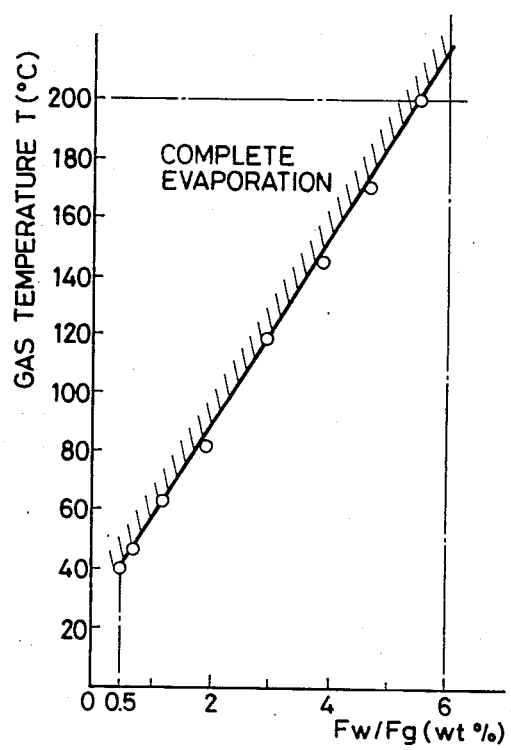
FIG. 4 is a graphical illustration of a relationship between an evaporation rate and a weight/flow rate ratio.
Figure 5:
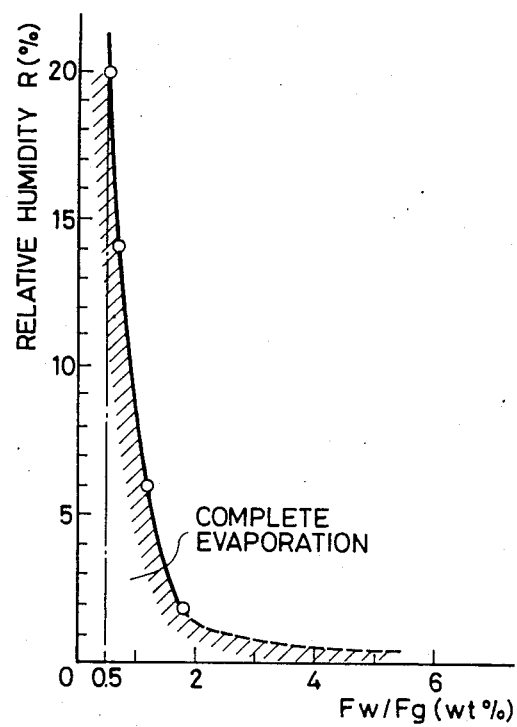
FIG. 5 is a graphical illustration of a variation of a total evaporation with respect to relative humidity of gas and flow rate ratio.

It is important that all the liquid injected into the chamber 11 is evaporated. Therefore, the conditions necessary for complete evaporation have been investigated, and the results of experiments are shown in FIGS. 3, 4, and 5. FIG. 3 shows the relationship between the evaporation rate X (%) and the weight/flow rate ratio (fw/fg) of the liquid (water) and the gas (air). The evaporation rate X is defined as follows:

$$\text{Evaporation rate } X = \frac{\text{Amount of Evaporation}}{\text{Amount of Atomization}} \times 100$$

Although an increase in the heating of the gas by the heater 16 increases the vaporization rate, the vaporization gas temperature at the outlet of the nozzle 12 becomes high, so that a heater input of about 150 W is normally a practical limit. FIG. 3 shows the variation in evaporation rate X with weight/flow rate ratio, for different heater inputs, and it can be seen from FIG. 3 that the weight/flow rate should preferably be less than 6 wt %. The practical lower limit is about 0.5 wt %, taking into account the amount of carrier gas used, the increase in heater energy required, and the increase in measurement time due to reduction in the number of particles in a given volume.

Next, investigation was made between the relationship between the weight/flow rate ratio fw/fg and the temperature of the gas, taking into account that all the liquid must be evaporated. FIG. 4 shows the results, and it can be seen that a temperature of at least 40° C. is necessary for weight/flow rate ratios within the range determined above.

Investigation was also made of the variation in weight/flow rate ratio fw/fg with the relative humidity R of the gas. and, as shown in FIG. 5 the relative humidity R must be less than 20% for satisfactory operation over the range of weight/flow rate ratios determined above.

Figure 2:
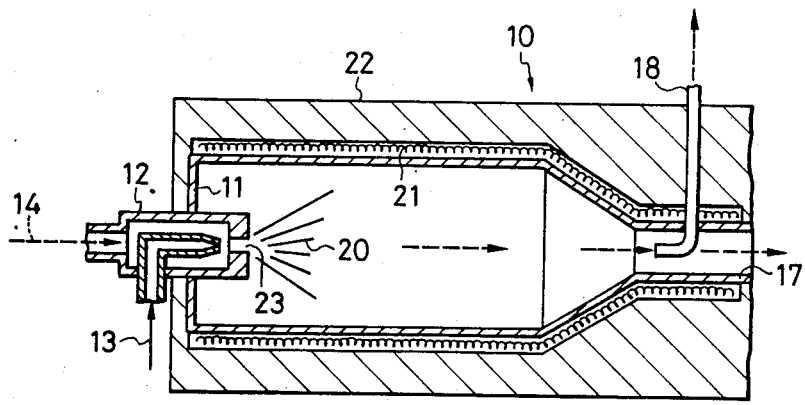
FIG. 2 is a schematic cross-sectional view of another embodiment of a purity detector constructed in accordance with the present invention.

It is also important that the liquid evaporated does not re-condense within the chamber 11. With suitable gas temperatures and flow rates it is possible to prevent this, but to reduce the risk of condensation, the impurity detector 10 of FIG. 1 may be modified as shown in FIG. 2. As illustrated in FIG. 2 the chamber 11 is surrounded by a heater coil 21, with an insulation layer 22 surrounding the heater coil 21. The heater coil 21 ensures that the temperature in the chamber 11 is maintained sufficiently high to prevent recondensation of the liquid and, if the temperature of the chamber 11 is sufficiently high, it is unnecessary to heat the gas fed to the nozzle 12 via conduit 14. Although there may be a slight delay between atomization and evaporation, the temperature in the chamber 11 produced by the heater 21, may still be sufficiently high to ensure that all the liquid is evaporated prior to reaching the duct 18 and the particle detector 19.

Other methods of causing evaporation of the gas may also be used such as, for example, infra-red heating, or application of high frequency energy to the water droplets.

Figure 6:
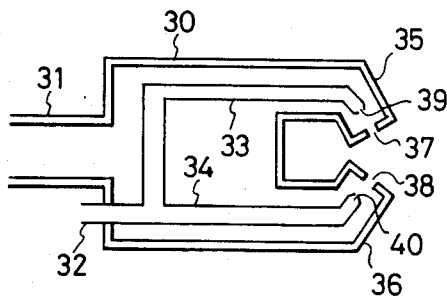
FIG. 6 is a schematic view of a two outlet nozzle system for use in a purification system of the present invention.

As illustrated in FIGS. 1 and 2, the nozzle 11 has a single outlet orifice 23. However, as shown in FIG. 6, a nozzle 30 is provided having an inlet 31 for connection to the conduit 14 for the gas, and a second inlet 32, for connection to the conduit 13 for the water. The ducting from the inlet 32 is divided into two branches 33, 34, each of which extends within a separate arm 35, 36 of the nozzle 30, with an interior of the arms 35, 36 communicating with the inlet 31. Each of the arms 35, 36 terminates in an orifice 37, 38 through which the liquid is expelled under the influence of the gas pressure from outlets 39, 40 of the branches 33, 34. The ends of the arms 35, 36 are inclined relative to each other, so that jets of liquid ejected from the orifices 37, 38 intersect each other. It has been found that this causes further atomization of the liquid, increasing the overall efficiency of the nozzle 30.

Figure 7:
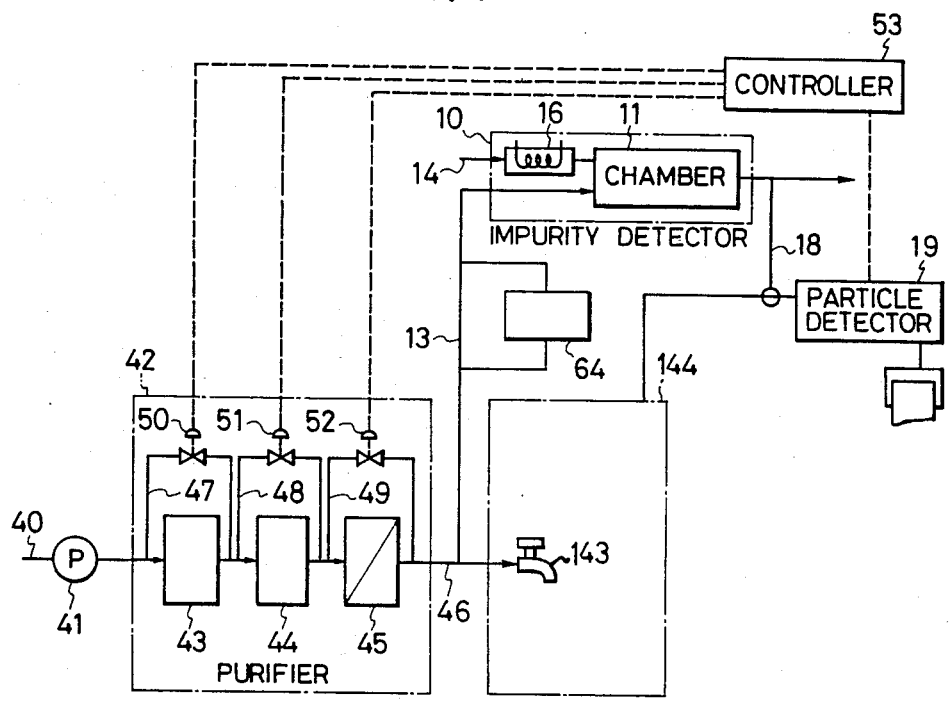
FIG. 7 is a schematic view of a water purification system employing the impurity detector of FIG. 1.

FIG. 7 shows an impurity detector 10 according to the present invention within a water purification system wherein water from an inlet 40 is pumped by a pump 41 through a purification system 42 to an outlet 143 within an area 144 in which the water is to be used. As is shown in FIG. 7, water entering the purification 42, passes first to a ultra-violet ray sterilizer 43 which kills any bacteria present in the water and then passes to a polisher 44 which removes soluble inorganic matter, and finally to an ultra-filter 45 which removes microorganisms and fine particles, and macromolecular soluble organic substances. The ultra-pure water produced is then passed via a duct 46 to the outlet 143. The conduit 13 which conveys the ultra-pure water to the impurity detector 10, is formed as a branch of the conduit 46. Feedback loops 47, 48 and 49 are connected from the outlet to the inlet of the sterilizer 43, the polisher 44, and the ultra-filter 45, respectively. Each feedback loop 47, 48 and 49, contains a valve 50, 51 and 52, respectively, the opening and closing of which is controlled via a control unit 53. The control unit 53 is also connected to the particle detector 19, and, when the particle detector 19 indicates that the impurity concentration has risen, the control unit 53 causes an opening of the valves 50, 51 and 52 to cause water to be fed back around the feedback loops 47, 48 and 49, thereby forming a circulatory loop to increase the sterilization, polishing, and ultra-filtration, before the water reaches the conduit 46. The use of three different valves 50, 51, and 52 permits the control unit 53 to modify the purification operations performed by the purifier 42 in dependence upon the impurity detected by the particle detector 19.

Figure 8:
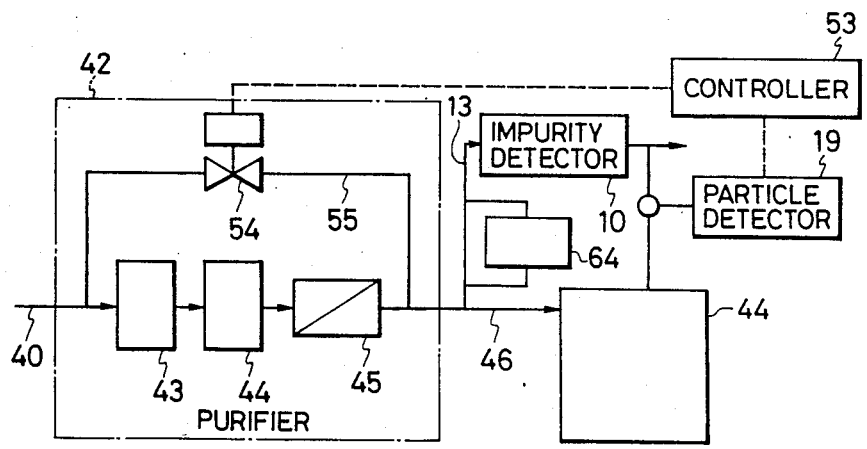
FIG. 8 is a schematic view of a modification of the water purification system of FIG. 7.

FIG. 8, provides a simplification of the system of FIG. 7, since single valve 54 is connected in a feedback loop 55 extending from the outlet of the ultra-filter 45 to the inlet of the sterilizer 43. The rest of the system of FIG. 8 is generally similar to the arrangement shown in FIG. 7.

Figure 9:
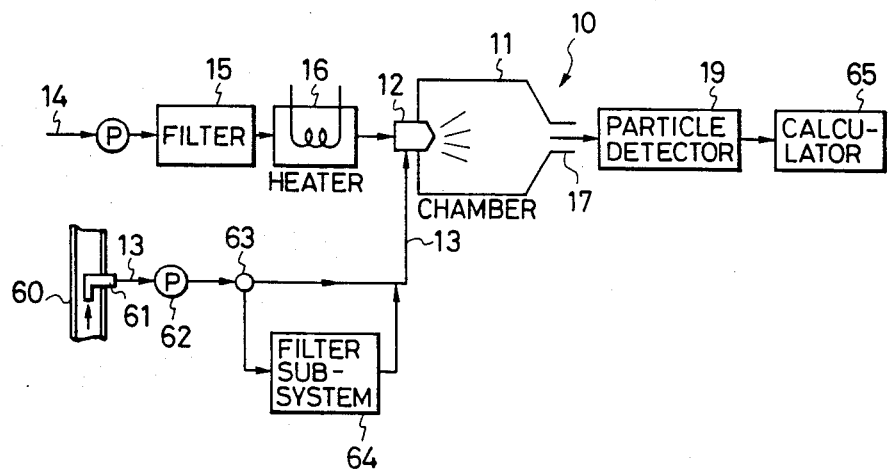
FIG. 9 is a schematic view of another embodiment of a water purification system of the present invention.

In the system of FIG. 9 ultra pure water in a conduit 60 (e.g. to some suitable outlet) is sampled via an inlet 61 and fed to the conduit 13 extending to the nozzle 12 of the chamber 11 of the impurity detector. A pump 62 is provided in the conduit 13 to deliver the water to the nozzle 12, with the conduit 13 also having a valve 63 therein for selectively either allowing the water to directly pass to the nozzle 12, or be diverted via a filter sub-system 64, prior to returning to the conduit 13. The filter sub-system 64 removes fine particles in the water by a membrane filter having a suitable porosity of a diameter 1 μm, and thus the quantities of the granular impurities in the water can be obtained by determining the difference in results when the water has passed through the filter sub-system 64, and when it has not.

Figure 10:
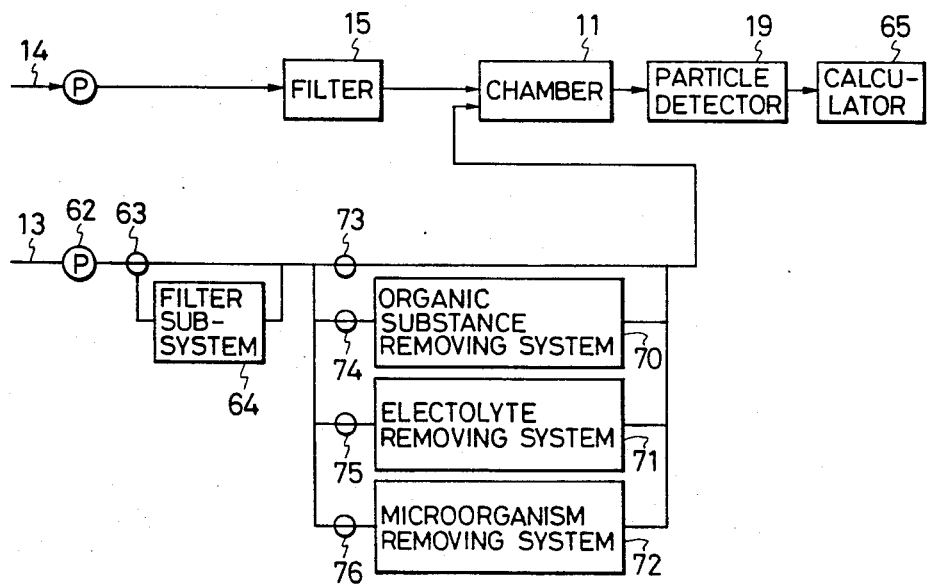
FIG. 10 is a schematic view of yet another embodiment of a water purification system of the present invention.

In use, the valve 63 is first set so as to allow ultra-pure water directly to the nozzle 12, and the particles in the water are measured by the particle detector 19. A calculating unit 65 then determines the total volume V1 of particles. Then the valve 63 directs the water via the filter sub-system 64, and the detector 19 measures the impurities then present in the water. The calculator 65 then calculates the total volume V2 of the particles. Thus, the volume of soluble impurities corresponds to the second measurement V2, while the total amount of granular impurities is the difference between the first measurement V1 and the second measurement V2. As shown in FIG. 10, three further filtration systems are provided, with a system 70 removing organic substances, a system 71 removing electrolytes, and a system 72 removing microorganisms. These three systems 70, 71 and 72 are disposed in parallel with the conduit 13 to the chamber 11, and the flow of water through the systems 70, 71, 72 is controlled by valves 73, 74, 75 and 76. By measuring the differences between the volumes obtained by the calculator unit 65 when the water is fed directly to the chamber 11, when it passes filtration sub-system 64, or when it is passed through any of systems 70, 71 and 72, the amounts of organic substances, electrolytes, and microorganisms can be measured.

The system 70 for removing organic substances may be based on activated carbon, but it is preferable that it is based on oxidation with ozone or ultra-violet light as this causes less contamination. Electrolytes can be removed by the system 71 by using an iron removing method involving an iron exchange resin, or an iron exchange membrane, but there is a risk of contamination due to impurities in the resin. It is even more difficult to provide a suitable microorganism removal system 72, the most promising systems being filtration.

Three experiments will now be described in which the impurities present in several types of water was measured using the system shown in FIG. 9.

EXPERIMENT 1

Underground water having a total concentration of evaporated residues of 30 ppm was diluted in pure water (the total evaporated residue was estimated to be several ppb), and water of various concentrations was atomizsed and vaporized using clean air at a temperature of 80° C. The particle diameter and the number of solid particles produced having a diameter greater than 0.1 $\mu$m were then determined using the laser scattering detector. The result showed that good correlations between the concentration C and the total volume V of impurities occurred at concentrations of around 10 ppb, and that the total evaporated residue could be determined by the total volume V.

EXPERIMENT 2

Sodium chloride, representing electrolytic contained in water, was diluted in a similar way as in experiment 1. After measurement of the water in various concentrations, under the same conditions as experiment 1, it was found that good correlations were found between the total volume V and the concentration C.

EXPERIMENT 3

Glucose, representing organic substances contained in water, was diluted and measured in a similar way to experiment 1 and 2. Again, it was found that a good correlation was obtained between the total volume V and the concentration C.

The results of these three experiments are shown graphically in FIG. 11. The results from experiment 1 are indicated by the open circles, joined by a solid line 80, the results from experiment 3 indicated by the solid circles joined by a dash line, and the results from experiment 2 indicated by triangles joined by a dot and dash line 82. The results for "pure" water (water containing no detectable impurities) is indicated by line 83.

Thus, according to the present invention as described above, it is possible to carry out on-line measurements of the concentrations of impurities in a liquid such as water. The impurities that can be measured include not only particles suspended in the water, but also dissolved salts and microorganisms making possible a comprehensive waterquality assessment which, until now, has not been possible. Furthermore, monitoring of water quality, and controlling that quality by feedback to the filtration arrangement from the particle detector, makes it possible to produce high-purity water on a continuous, and stable, basis.

The present invention also makes it possible to measure impurities in high-purity water using a single instrument, rather than several measuring instruments as has previously been required.

What is claimed is:

1. An impurity detector for liquid, the impurity detector comorising:

an evaporation chamber for a liquid sample;
   at least one atomizing nozzle mounted on said evaporation chamber for injection of a liquid sample into said evaporation chamber with a gas to form an atomized liquid;
   means for heating the liquid to effect evaporation in said evaporation chamber of all the atomized liquid;
   a detector region to which said evaporation chamber is connected in a substantially closed manner so that all the gas and all the solid impurity particles entrained in the gas due to the evaporation of the liquid pass from said evaporation chamber to said detector region; and
   a particle detector communicating with said detector region adapted to measure the number and size of the impurity particles in the gas.

2. An impurity detector according to claim 1, wherein said means for heating the liquid comprises a heater means for heating said gas, said liquid being heated by said gas in said evaporation chamber.

3. An impurity detector according to claim 1 including a heater means surrounding said chamber.

4. An impurity detector according to claim 1, wherein said particle detector is a dispersed laser beam detector.

5. An impurity detector according to claim 1, having an inlet for said liquid sample, and a duct connecting said inlet to said atomizing nozzle, said duct having a first branch providing a direct passage from said inlet to said atomizing nozzle, and a second branch containing a filter.

6. A high-purity water system, comprising:
   a filtration unit having an inlet duct for receiving water, an outlet duct, and at least one filter system for purifying said water, said at least one filter system having an inlet communicating with said inlet duct and an outlet communicating with said outlet duct, a feedback duct connected between said outlet and said inlet of said at least one filter system for returning at least some of said water from said outlet to said inlet of said at least one filter system, and a valve in said feedback duct for controlling flow of said at least some of said water through said feedback duct;
   a dispenser for water connected to said outlet duct;
   an impurity detector also connected to said outlet duct, said impurity detector comprising an evaporation chamber for a sample of said water, at least one atomizing nozzle for injection of the water sample into the chamber with a gas;
   means for heating the water to effect evaporation in said chamber of all the atomized water;
   a detector region to which the chamber is connected in a substantially closed manner so that all the gas and all the solid impurity particles entrained in the gas due to the evaporation of the water pass from the chamber to the detector region;
   a particle detector at the detector region adapted to measure the number and size of the impurity particles in the gas; and
   a controller unit connected to said particle detector and said valve;
   thereby to permit said controller unit to regulate said flow of water through said feedback duct by control of said valve in dependence upon the number and size of particles detected by said particle detector.

7. A method of measuring the number and size of impurities in a liquid sample, the method comrising the steps of:

atomizing the liquid sample by injecting the liquid sample from a liquid source with gas from a gas source into an evaporation chamber through at least one nozzle means to form an atomized liquid;

evaporating the atomized liquid in said evaporation chamber by heating the atomized liquid at substantially the same time as atomization of the liquid sample, so that solid impurity particles in the liquid sample are entrained in the gas;

passing all the gas having the solid impurity particles entrained therein to a detector region; and measuring the number and size of the solid impurity particles in the gas at the detector region by a particle detector means.

8. A method according to claim 7, wherein said gas is heated prior to said atomization step, said liquid being evaporated due to heat transfer from said gas.

9. A method according to claim 8, wherein said gas is heated to a temperature not less than 40° C.

10. A method according to claim 7, wherein the weight/flow rate ratio of said liquid and said gas is between 0.5 wt % and 6 wt %.

11. An impurity detector for a liquid, the impurity detector comprising:

an evaporation chamber for a liquid sample, said evaporation chamber having an inlet and a detector region remote from said inlet;

an atomizing nozzle provided for said evaporation chamber to form said inlet for the liquid sample for atomizing the liquid sample by injecting the liquid sample together with a gas into said evaporation chamber;

liquid passage means connected both to said atomizing nozzle and to a liquid source for introducing a liquid from said liquid source into said atomizing nozzle;

gas passage means connected both to said atomizing nozzle and to a gas source for introducing a gas from the gas source into said atomizing nozzle;

heating means for heating said liquid sample to evaporate all of the atomized liquid in said evaporation chamber so that solid impurity particles in said liquid sample are entrained in the gas; and particle detector means communicating with said detector region for measuring the number and size of the solid impurity particles in the gas.

12. An impurity detector according to claim 11, further comprising:

a branch passage branching from said liquid passage means at a first point and joined to said liquid passage means at a second point downstream of said first point;

valve means for switching a liquid passage to said atomizing nozzle between said branch passage and said liquid passage means positioned between said first and second points; and a calculating means for determining a total volume of particles according to a measurement signal supplied by said particle detector means.

13. An impurity detector according to claim 12, further comprising filtration means including a plurality of valves provided in parallel with the liquid passage means, said filtration means including a means for removing organic substances, a means for removing electrolytes, and a means for removing micro-organisms.

14. A high purity water system, the system comprising:

a purification means for purifying water from a water source, said purification means including a feedback loop and a control valve means provided on said feedback loop for controlling a flow rate of water flowing in said feedback loop;

an impurity detector means connected to said purification means by a duct for introducing a water sample into said impurity detector means, said impurity detector means including an evaporation chamber means for accommodating a sample of the water, an atomizing nozzle means for injecting the water sample with air into said evaporator chamber means to form an atomized water sample, a heating means for heating said water sample to evaporate said atomized water sample in said evaporator chamber means to entrain solid impurity particles in gases, and a detector region to which said evaporation chamber means is connected in a substantially closed manner so that all the gases and all the solid impurity particles entrained in the gases due to evaporation of the water sample pass from said evaporation chamber means to said detector region, and a particle detector means communicating with said detector region for measuring a number and size of the impurity particles in the gases, and a controller means connected to said particle detector means and said control valve means for controlling said control valve means in dependence upon an output signal reflecting a measuring result by said particle detector means.

15. A high purity water system according to claim 14, wherein said feedback loop bridges a downstream side and upstream side of said means.

* * * * *